United States Patent
Ariola, Jr. et al.

(10) Patent No.: US 8,656,585 B2
(45) Date of Patent: Feb. 25, 2014

(54) PROCESS FOR MANUFACTURING ELECTROSURGICAL FORCEPS WITH COMPOSITE MATERIAL TIPS

(75) Inventors: John P. Ariola, Jr., Norton, MA (US); Lawrence T. Kirwan, Jr., Pembroke, MA (US)

(73) Assignee: Kirwan Surgical Products LLC, Marshfield, MA (US)

(*) Notice: Subject to any disclaimer, the term of this patent is extended or adjusted under 35 U.S.C. 154(b) by 231 days.

(21) Appl. No.: 13/312,195

(22) Filed: Dec. 6, 2011

(65) Prior Publication Data
US 2012/0073130 A1    Mar. 29, 2012

Related U.S. Application Data

(62) Division of application No. 12/398,685, filed on Mar. 5, 2009, now Pat. No. 8,108,994, which is a division of application No. 11/430,567, filed on May 9, 2006, now Pat. No. 7,789,882.

(51) Int. Cl.
*H01R 43/00* (2006.01)
*H05K 13/00* (2006.01)

(52) U.S. Cl.
USPC ............... 29/854; 29/825; 29/857; 29/874

(58) Field of Classification Search
USPC ......... 29/854, 825, 857, 874, 876; 606/50–52
See application file for complete search history.

(56) References Cited

U.S. PATENT DOCUMENTS

| | | |
|---|---|---|
| 3,685,518 A | 8/1972 | Beuerle et al. |
| 3,755,164 A | 8/1973 | Van Wyk |
| 4,427,006 A | 1/1984 | Nottke |
| 4,492,231 A | 1/1985 | Auth |
| 5,196,009 A | 3/1993 | Kirwan, Jr. |
| 5,624,475 A | 4/1997 | Nadkarni et al. |
| 5,759,183 A | 6/1998 | VanDusseldorp |
| 5,891,142 A | 4/1999 | Eggers et al. |
| 5,924,983 A | 7/1999 | Takaki et al. |
| 6,241,723 B1 | 6/2001 | Heim et al. |
| 6,293,946 B1 | 9/2001 | Thorne |
| 6,296,637 B1 | 10/2001 | Thorne |
| 6,298,550 B1 | 10/2001 | Kirwan, Jr. |
| 6,413,255 B1 | 7/2002 | Stern |
| 6,533,781 B2 | 3/2003 | Heim et al. |
| 6,558,382 B2 | 5/2003 | Jahns et al. |
| 6,638,274 B2 | 10/2003 | Yamamoto |
| 6,747,610 B1 | 6/2004 | Taima et al. |
| 6,749,610 B2 | 6/2004 | Kirwan, Jr. et al. |
| 6,994,245 B2 | 2/2006 | Pinchot |
| 7,235,073 B2 | 6/2007 | Levine et al. |
| 2001/0018587 A1 | 8/2001 | Yamamoto |
| 2003/0130653 A1 | 7/2003 | Sixto et al. |
| 2004/0116792 A1 | 6/2004 | Nesbit |
| 2005/0033286 A1 | 2/2005 | Eggers et al. |

FOREIGN PATENT DOCUMENTS

| | | |
|---|---|---|
| EP | 1120797 | 1/2001 |
| JP | 05386622 | 7/1978 |

*Primary Examiner* — Thiem Phan
(74) *Attorney, Agent, or Firm* — Preti Flaherty Beliveau & Pachios LLP

(57) ABSTRACT

An electrosurgical forceps has at least the tip of one blade member formed of a composite material having aligned elongated particles of nickel interspersed in a matrix of silver particles. The tip can be provided as a tip member attached, such as by brazing, to the body of the blade member, or the entire blade member can be formed of the silver/nickel composite material. In another embodiment, the tip or blade member is formed of a dispersion strengthened silver or copper composite material.

4 Claims, 3 Drawing Sheets

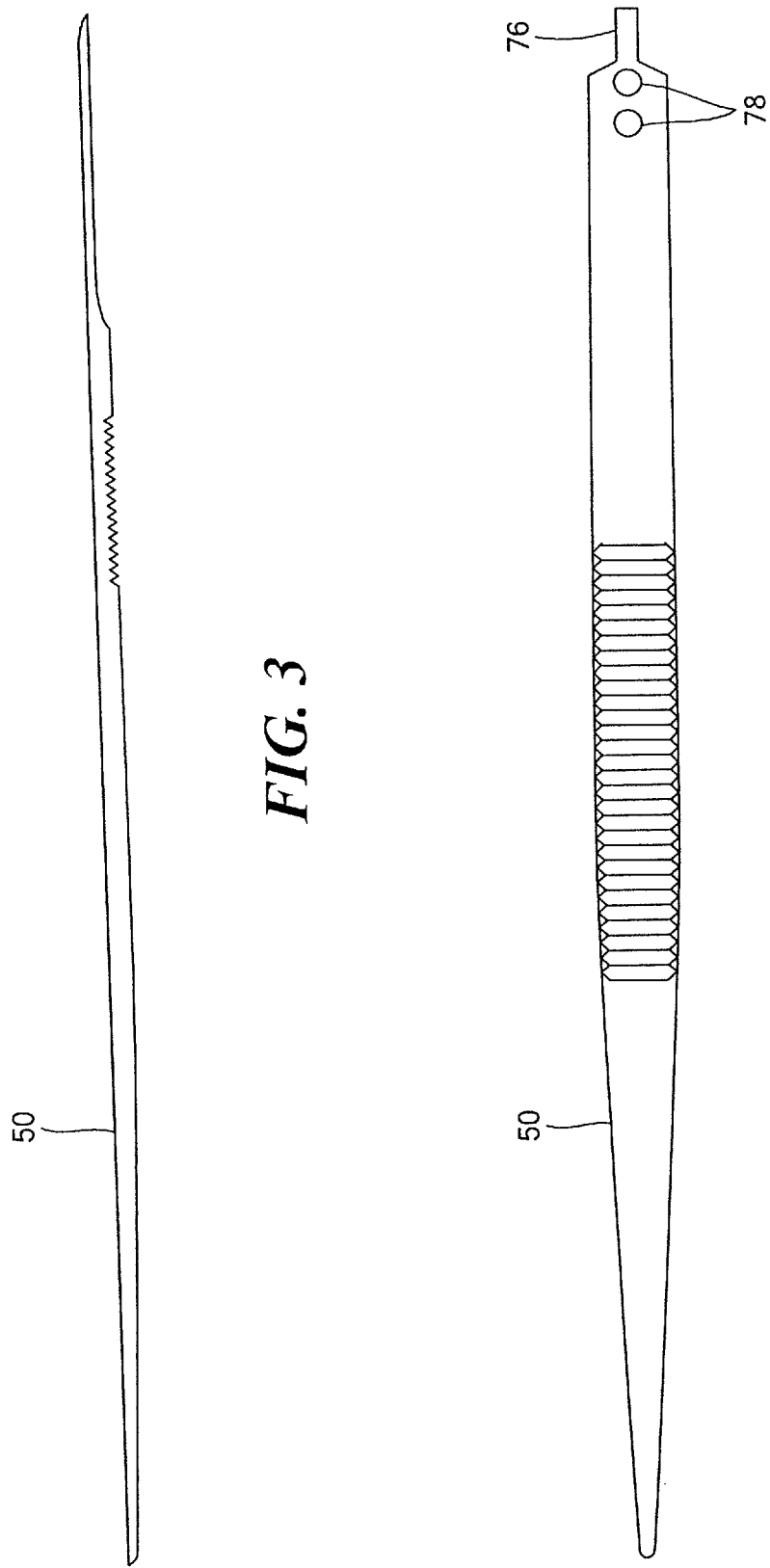

PROCESS FOR MANUFACTURING ELECTROSURGICAL FORCEPS WITH COMPOSITE MATERIAL TIPS

CROSS REFERENCE TO RELATED APPLICATIONS

This application is a division of U.S. patent application Ser. No. 12/398,685, filed Mar. 5, 2009, entitled "Process for Manufacturing Electrosurgical Forceps With Composite Material Tips," which is a division of U.S. patent application Ser. No. 11/430,567, filed May 9, 2006, now U.S. Pat. No. 7,789,882, issued Sep. 7, 2010, entitled "Electrosurgical Forceps with Composite Material Tips," the disclosures of which are incorporated by reference herein.

STATEMENT REGARDING FEDERALLY SPONSORED RESEARCH OR DEVELOPMENT

N/A

BACKGROUND OF THE INVENTION

Electro-surgical forceps have a pair of resilient blades or arms that are used for grasping and coagulating tissue. The forceps may be monopolar or bipolar. In monopolar forceps, the blades are welded or otherwise joined to form an electrode in electrical communication with an electrical generator. Current flows from the active electrode through the patient's tissue to a dispersive electrode in contact with the patient's skin (which may be at some distance from the forceps) and back to the generator. In bipolar forceps, each blade of the pair comprises an electrode in communication with an electrical generator. Current flows from one blade through the tissue to the other blade.

In some instances, tissue may adhere or stick to the tips of the blades. If sticking occurs, the surgeon must pull on the forceps to release it from the tissue, possibly causing further bleeding and requiring that the forceps be cleaned. It is known to prevent or minimize such sticking of tissue to electrosurgical forceps by manufacturing the blades of the forceps from nickel. See U.S. Pat. No. 5,196,009. Other materials, such as silver or silver alloys, have also been used to dissipate heat and minimize or prevent sticking. See U.S. Pat. Nos. 3,685,518 and 6,749,610.

SUMMARY OF THE INVENTION

Electro-surgical forceps are provided which minimize or prevent sticking to the tissue of a patient and eschar buildup. The forceps include a pair of blade members extending from an insulated cap portion to a tip. At least one of the blade members is electrically conducting. Within the cap portion, the blades are electrically connected to terminals for connection to an electrical generator. At least the tip of the blade member is comprised of a silver/nickel composite material. The silver/nickel composite material is comprised of elongated nickel particles interspersed in a matrix of silver particles. The elongated nickel particles are aligned with each other and with a longitudinal axis of the tip member. The tip is operative to dissipate heat generated at the tip to prevent sticking of tissue to the forceps during use and to allow operation of the forceps at a lower power level. In one embodiment, a blade member includes a body or handle of a material such as stainless steel and a tip member comprised of the silver/nickel composite material. In another embodiment, the entire blade member is comprised of the silver/nickel composite material. Forceps incorporating a tip comprised of the silver/nickel composite material are simple to manufacture. The tip is formed from a single solid piece of material, which eliminates problems with coatings and platings that may be prone to wear or delamination. The silver/nickel composite material is slightly softer than steel but substantially harder than pure silver, resulting in a tip that is durable without the need for additional work hardening required with pure silver. In yet another embodiment, the forceps can incorporate a tip or blade formed of a dispersion strengthened silver or copper composite material. The dispersion strengthened silver or copper includes particles of alumina, $Al_2O_3$, dispersed within a matrix of silver or copper.

DESCRIPTION OF THE DRAWINGS

The invention will be more fully understood from the following detailed description taken in conjunction with the accompanying drawings in which:

FIG. 3 is a top view of a further embodiment of electrosurgical forceps according to the invention;

FIG. 4 is a side view of the electrosurgical forceps of FIG. 3;

DETAILED DESCRIPTION OF THE INVENTION

The disclosures of U.S. patent application Ser. No. 12/398,685, filed Mar. 5, 2009, entitled "Process for Manufacturing Electrosurgical Forceps With Composite Material Tips," and U.S. patent application Ser. No. 11/430,567, filed May 9, 2006, now U.S. Pat. No. 7,789,882, issued Sep. 7, 2010, entitled "Electrosurgical Forceps with Composite Material Tips," are incorporated by reference herein.

Figure 1:
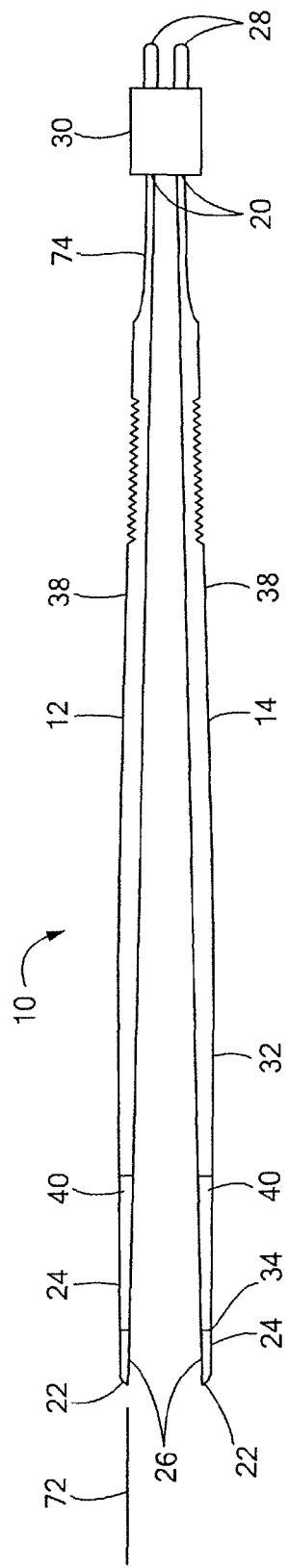
FIG. 1 is a top view of a first embodiment of electrosurgical forceps according to the present invention.
Figure 2:
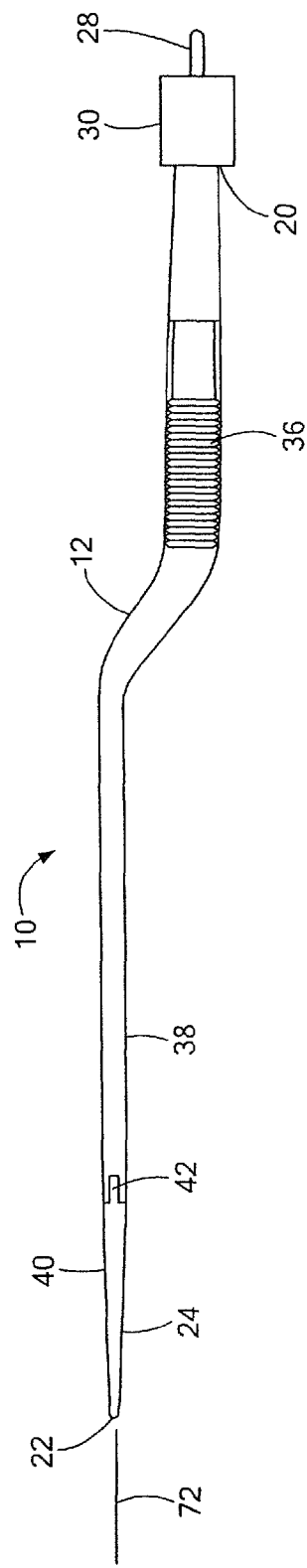
FIG. 2 is a side view of the electrosurgical forceps of FIG. 1.

Referring to FIGS. 1 and 2, a bipolar forceps 10 has first and second blade or electrode members 12 and 14. Each of the blade members is elongated and extends from a first end 20 to a second end 22 at a tip 24. The blade members are generally flat, and the tips are configured for gripping tissue between opposed surfaces 26. The first ends 20 are electrically connected in any suitable manner, such as by crimping, welding, or soldering, to terminal pins 28. First ends 20 along with the terminal pins 24 are encapsulated using an epoxy based material or otherwise mounted within an insulating cap portion 30. The blade members may be insulated with an insulating material 32 along most of their length from the cap portion 30 to a location 34 close to the tip.

Alternatively, the blade members may be uninsulated. Serrated finger grips 36 may be formed in each blade member to aid the physician in gripping the forceps during use. A plating of an electrically and thermally conductive biocompatible material such as gold may be provided on the tip 24 of an insulated blade member and over the tip or over the entire body of an uninsulated blade member.

In the embodiment illustrated in FIGS. 1 and 2, the blade member includes a body 38 or handle and a tip member 40 attached to the body. The body is comprised of a material, such as stainless steel or nickel, that provides suitable strength and electrical conductivity. The tip member is comprised of a composite material of silver and nickel. (There is no alloy of nickel and silver, because the solubility of nickel into silver is limited, less than 0.12 weight percent, depending on the process).

The tip member is attached to the body in any suitable manner to facilitate electrical conductivity between the body and the tip member and to withstand breakage under typical usage. Brazing the tip member to the body is a suitable manner of attachment. Preferably, the tip member is formed with a tab 42 that fits within a corresponding recess in the body. Alternatively, the tip member and body may include a dovetail joint that may be force fit together, requiring no brazing. A further alternative includes a lap joint that is welded or bonded with conductive epoxy. FIGS. 3 and 4 illustrate a further embodiment in which the entire blade member 50 is comprised of the silver/nickel composite material.

The silver/nickel composite material is comprised of nickel particles interspersed in a matrix of silver particles. The silver gives the material good thermal and electrical conductivity. The addition of a small amount of nickel to the silver enhances the mechanical properties when compared to pure silver.

| Property | Commercially pure silver | 90% Ag/ 10% Ni | Dispersion Strengthened Copper (Cu/~.30% $Al_2O_3$) | Dispersion Strengthened Silver (Ag/.25% $Al_2O_3$) |
| --- | --- | --- | --- | --- |
| Density ($g/cm^3$) | 10.49 | 10.3 | 8.81 | 10.4 (approx.) |
| Tensile Strength (MPa) | 125 | 240 | 462-614 | 737 |
| Hardness (HV1) | 25-27 ($R_B$) | 50 ($R_B$) | | 95 ($R_B$) |
| Elongation (%) | 54 | 38 | 20 | 8 |
| Conductivity ($m/\Omega/mm^2$) | 61 (approx.) | 50 (approx.) | | |
| Conductivity (% IACS) | 105 | 86 (approx.) | 89 | 85 |

The nickel content of the silver/nickel composite material can range from 5 wt. % to 40 wt. %. Less nickel results in a material with a greater electrical conductivity and lesser hardness and tensile strength. More nickel results in a material with a lesser electrical conductivity and greater hardness and tensile strength. In the presently preferred embodiment, a blend of 10 wt. % nickel to 90 wt. % silver is provided.

In another embodiment, the forceps can incorporate a tip or blade member formed of a dispersion strengthened silver or copper composite material. The dispersion strengthened silver or copper includes particles of aluminum oxide, $Al_2O_3$ (alumina), dispersed within a matrix of silver or copper. In dispersion strengthened silver, the aluminum oxide ranges from 0.1 to 0.5 wt. %, the balance being silver. In dispersion strengthened copper, the aluminum oxide ranges from 0.3 to 1.1 wt. %, the balance being copper. This material provides increased hardness as well as good electrical conductivity. The table also illustrates some properties of dispersion strengthened copper and silver.

Figure 5:
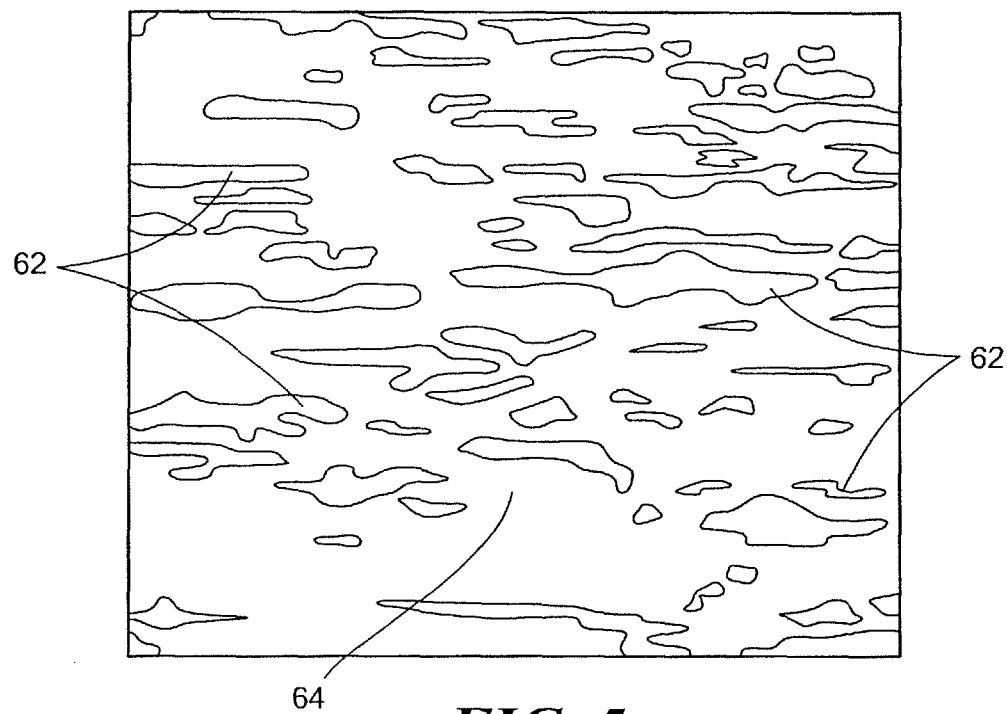
FIG. 5 is a longitudinal section illustrating the microstructure of a silver/nickel composite material used for the present electrosurgical forceps.
Figure 6:
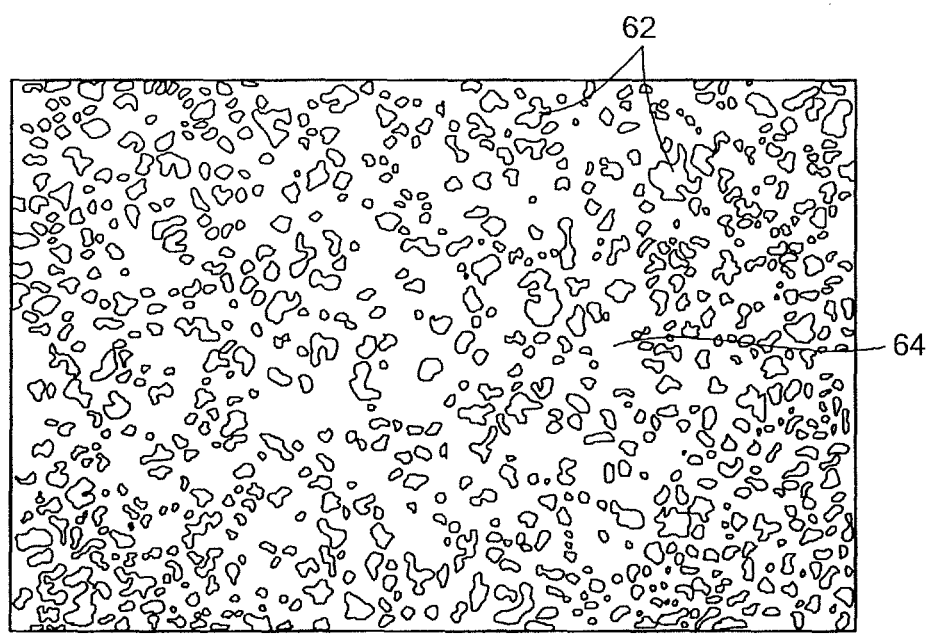
FIG. 6 is a cross section illustrating the microstructure of the silver/nickel composite material of FIG. 5.

The silver/nickel composite material is formed by blending powders of silver and nickel particles. The particle size is preferably in the powder range, 1 to 100 μm. If the particle size is less than 1 μm, the material is difficult to deform (difficult to work harden), and if the particle size is greater than 100 μm, distribution of the different components in the matrix is difficult to control. The blended powders are compacted and sintered to form a sintered body. The sintered body is then extruded as a sheet, which deforms the nickel particles along the direction of the extrusion. FIG. 5 illustrates a longitudinal section in which nickel particles 62 can be seen extending generally parallel to the direction of extrusion among a matrix of silver particles 64. FIG. 6 illustrates a cross section perpendicular to the direction of extrusion.

After extrusion, the material is drawn or rolled to achieve the desired final thickness dimension. The tip member 40, or the entire blade member 12 or 14, is stamped or otherwise formed from the drawn or rolled material. The tip member or blade member is stamped such that the direction of elongation of the nickel particles 62 is aligned with a longitudinal axis 72 of the tip member or the blade. The elongated nickel "fibers" are more pronounced in this orientation. Most likely, work hardened nickel fibers add to the modulus and make it stiffer in the bending direction. If the tip member is formed separately from the body, the tip member is attached to the body, for example, by brazing.

The forceps are then manufactured in any suitable manner. For example, serrations 36 are stamped into a mid portion of the blade member. The rear or spring section 74 is cold formed, as by rolling, to compress its thickness and to work harden the material. Work hardening of the material in this section strengthens the material, enabling a physician to squeeze the blades together repeatedly to grasp tissue and release the blades to return to their rest position. The perimeter of the strip is stamped to form the general shape of the blade member. As indicated in FIGS. 3-4, the blade member could have a generally straight configuration, or as indicated in FIGS. 1-2, the blade member could have bends along its length, depending on the particular application. The perimeter of the blade member is formed, as by a coining process, to form the edges. A tab 76 is stamped, deburred, and formed at the end of the blade member. See FIG. 4. The terminal pins may be attached to the tabs in any suitable manner, such as by crimping, welding, or soldering. Holes 78 may be stamped into the end. The holes allow epoxy or other appropriate potting material to flow through and around the blade members to fix the blade members more firmly within the cap portion.

Preferably, the tip is plated with a thin layer of an electrically and thermally conducting, biocompatible material, such as gold, using conventional plating processes. Alternatively, for uninsulated forceps the entire body is plated. For example, the thickness of the layer generally ranges from 0.0001 to 0.001 inches, and is typically about 0.0004 inches. A gold layer prevents tarnishing of the material(s) beneath it. The gold layer may be made from a variety of gold alloys. Preferably, the gold layer is made from 24 carat hard gold. Other electrically and thermally conductive materials that are biocompatible with human tissue, such as rhodium, may be used.

If desired, the blade member may be encapsulated in insulating material, such as a plastic material capable of withstanding the high temperatures generated during use. The insulation may be formed in any suitable manner, such as by spraying on a liquid which dries to form a solid coating. The tip of the blade member is left uninsulated for a suitable distance, such as ⅜ inch. The insulation is typically 0.010 to 0.015 inches thick.

The tip member or blade member of the present forceps is simple in design and simple to manufacture. Since the silver/nickel composite material has good mechanical and thermal properties, the tip member or the tip of the blade member can be made thin and small, comparable to standard forceps. Because the tip member or the blade member is formed from a single solid piece of material, the tip is the same composite material throughout. There is no coating material on the tip that may be prone to removal due to cleaning and polishing. Because the silver/nickel composite material is substantially harder and thus less ductile than pure silver, no additional processing is needed to make the material manufacturable. The composite material is slightly softer than steel, but substantially harder than pure silver, making the tip members more durable than electroplated forceps intended for reusable applications.

The dispersion strengthened silver and the dispersion strengthened copper composite materials are formed by melting together aluminum and silver or aluminum and copper. The melt is cooled and ground to a fine powder. The powder is formed into a desired shape and the material is heated so that the aluminum oxidizes, leaving a dispersion of very small aluminum oxide particles within the silver or copper base material. With this process, the aluminum oxide becomes uniformly dispersed within the matrix material. This material can then be formed into the tip member or blade member, as described above.

Although the invention has been particularly described with respect to bipolar forceps, it will be appreciated that the invention is equally applicable to monopolar forceps. Additionally, although it is preferable that both blades of the forceps be formed with the silver/nickel composite material described above, only one blade could be so formed if desired.

Electrosurgical forceps employing the silver/nickel composite material can be disposable or reusable.

The invention is not to be limited by what has been particularly shown and described, except as indicated by the appended claims.

What is claimed is:

1. A process for manufacturing electrosurgical forceps comprising:
   providing a dispersion strengthened silver or copper composite material comprised of aluminum oxide dispersed in a matrix of silver or copper, comprising:
      melting aluminum together with one of silver or copper to form a melt;
      cooling the melt to form a solid;
      grinding the solid into a powder; and
      heating the powder to oxidize the aluminum to aluminum oxide;
   forming a blade member or a tip member from the dispersion strengthened silver or copper material;
   forming the blade member or the tip member into a first electrosurgical forceps blade;
   providing a second electrosurgical forceps blade;
   connecting the first electrosurgical blade and the second electrosurgical blade to electrodes at a connection; and
   fixing the connection between the first electrosurgical blade, the second electrosurgical blade, and the electrodes within an insulating cap portion.

2. The process of claim 1, wherein the second electrosurgical forceps blade comprises at least a tip comprised of a composite material comprising particles of aluminum oxide dispersed in a matrix of silver or copper particles.

3. The process of claim 1, wherein the aluminum oxide content in silver ranges from 0.1 weight percent to 0.5 weight percent of the total, the balance comprising silver.

4. The process of claim 1, wherein the aluminum oxide content in copper ranges from 0.3 weight percent to 1.1 weight percent of the total, the balance comprising copper.

* * * * *